United States Patent [19]

Kaufhold

[11] Patent Number: 4,506,105
[45] Date of Patent: Mar. 19, 1985

[54] PROCESS FOR PREPARING CYCLOOCTENE-4-OL-1 FROM CYCLOOCTADIENE-1,5

[75] Inventor: Manfred Kaufhold, Marl, Fed. Rep. of Germany

[73] Assignee: Chemische Werke Hüls AG, Marl, Fed. Rep. of Germany

[21] Appl. No.: 519,895

[22] Filed: Aug. 4, 1983

Related U.S. Application Data

[63] Continuation of Ser. No. 303,584, Sep. 18, 1981.

[30] Foreign Application Priority Data

Oct. 1, 1980 [DE] Fed. Rep. of Germany ....... 3037093

[51] Int. Cl.$^3$ ..................... C07C 35/20; C07C 27/02
[52] U.S. Cl. .................................. 568/821; 560/231; 560/234
[58] Field of Search ................. 568/821; 560/234, 231

[56] References Cited

U.S. PATENT DOCUMENTS

| | | |
|---|---|---|
| 2,440,220 | 4/1948 | Bruson . |
| 2,764,610 | 9/1956 | Kuder . |
| 2,822,348 | 2/1958 | Haslam ........................... 560/234 X |
| 3,328,439 | 6/1967 | Hamilton ........................ 560/234 X |
| 3,413,336 | 11/1968 | Hulsmann et al. ............. 560/234 X |
| 3,609,182 | 9/1971 | Baker et al. .................... 568/821 |

OTHER PUBLICATIONS

Reimer et al, Jour. Amer. Chem. Soc., vol. 43, (1921), 945–949.
Cope et al, Jour. Amer. Chem. Soc., vol. 81, (1959), pp. 1643–1650.
Knight et al, Jour. Amer. Chem. Soc., vol. 75, (1953), pp. 6212–6215.
Harry Gibson, "Chemistry of Formic Acid etc.", Chemical Reviews, vol. 69, (1969), pp. 673–683.

*Primary Examiner*—Bernard Helfin
*Attorney, Agent, or Firm*—Wells & Wells

[57] ABSTRACT

A process for preparing cyclooctene-4-ol-1 with a content in excess of 70% by reacting cyclooctadiene-1,5 with formic acid and then saponifying or transesterifying the cyclooctenyl formate with an alcohol of low boiling point.

In the absence of a catalyst, formic acid is reacted with cyclooctadiene-1,5 at 50° to 200° C., preferably 95° to 105° C. The reaction product without further processing is directly distilled, and the formic acid ester so obtained is transesterified with an alcohol of low boiling point into the formate of that alcohol and into cyclooctene-4-ol-1.

16 Claims, No Drawings

PROCESS FOR PREPARING CYCLOOCTENE-4-OL-1 FROM CYCLOOCTADIENE-1,5

This application is a continuation of application Ser. No. 303,584, filed Sept. 18, 1981.

CROSS-REFERENCE TO A RELATED APPLICATION

Applicant claims priority under 35 USC 119 for application P 30 37 093.5 filed Oct. 1, 1980 in the Patent Office of the Federal Republic of Germany.

BACKGROUND OF THE INVENTION

The field of the invention is the preparation of unsaturated alcohols and the present invention is particularly concerned with the preparation of cyclooctene-4-ol-1.

A. C. Cope et al disclose the state of the art production of cyclooctene-4-ol-1 in the Journal of the American Chemical Society, Volume 81 (1959), pages 1643–1650, the disclosure of which is incorporated herein.

According to this state of the art, cyclooctene-4-ol-1 is prepared by adding 1 mole of formic acid in the presence of perchloric acid to 1 mole of cis-cis-1,5-cyclooctadiene in a first stage. Thereupon the reaction products are saponified and reprocessed by a careful fractional distillation. To separate the saturated alcohols, which are formed in large amounts, from the desired cyclooctene-4-ol-1, an expensive extraction with a 20% aqueous silver nitrate solution must be resorted to. The yield in cyclooctene-4-ol-1 in this costly process amounts to only 20%.

The uncatalyzed addition of formic acid to other olefins is known, though not to cyclooctadiene-1,5 as reported by H. B. Knight, R. E. Koos and D. Swern in the Journal of the American Chemical Society, Volume 75 (1953) at page 6212. As regards the uncatalyzed reaction, a conversion of only 80% is obtained after 24 hours at the boiling point of the formic acid. By adding slight amounts of perchloric acid (0.5 to 2% by weight referred to olefin), the reaction time can be reduced to 5 to 15 minutes.

1 Mol of vinylcyclohexene, which is an isomer of cyclooctadiene-1,5, reacts with 3 moles of formic acid according to the procedure disclosed in U.S. Pat. No. 2,764,610 (8 hours at 94° to 97° C. with reflux) with a conversion of 44%.

The yield in monoformic acid esters referred to the converted vinylcyclohexene amounts to only 61%.

Accordingly, all the prior art processes provide only slight yields, require long reaction times or make use of catalysts which require reprocessing and ecological problems.

SUMMARY OF THE INVENTION

Having in mind the limitations of the prior art, there exists therefore great interest in a process for producing a cyclooctene-4-ol-1 at low industrial cost and without long dwell times, at a content in excess of 70% and of high yields.

According to the present invention, cyclooctene-4-ol-1 with a content in excess of 70% is prepared by reacting cyclooctadiene-1,5 with formic acid and then saponifying or transesterifying the cyclooctenyl formate with an alcohol of low boiling point.

In the absence of a catalyst, the formic acid is reacted with the cyclooctadiene-1,5 at 50° to 200° C., preferably 95° to 105° C. and the reaction product without further processing is directly utilized. The formic acid ester so obtained is transesterified with an alcohol of low boiling point into the formate of that alcohol and into cyclooctene-4-ol-1. Cyclooctene-4-ol-1 is then separated by distillation.

DESCRIPTION OF THE PREFERRED EMBODIMENT

A reaction time between 1 and 20 hours, preferably between 8 and 12 hours, is required in the present invention for the reaction between formic acid and cyclooctadiene-1,5 without a catalyst.

From the so prepared cyclooctenyl formate the corresponding alcohol is produced by basic saponifying or by transesterifying. The saponifying is carried out by reacting the cyclooctenyl formate for instance with sodium hydroxide solution in this case with a solvent (alcohol).

The transesterification process useful in the present invention is disclosed in the Journal of the American Chemical Society, Volume 43 (1921), page 948, M. R. Downes; West German Published Application No. 12 46 720 and U.S. Pat. No. 2,440,220.

By low boiling point alcohol is meant an alcohol having a boiling point between 64 and 158 C. Examples of these low boiling point alcohols include: methanol, ethanol, propanol, iso-propanol, n-butanol, iso-butanol, tert.butanol, pentanole and hexanole.

It is new and unexpected that cyclooctene-4-ol-1 is obtained in contents exceeding 70% as determined by nuclear resonance spectroscopy and with good yields by reacting cyclooctadiene-1,5-without catalysts at temperatures of 50° to 200° C., preferably from 90° to 105° C., with formic acid. The formic acid ester is obtained without further processing, directly by distillation and this ester is transesterified conventionally with an alcohol of low boiling point into the formate of this alcohol and into cyclooctene-4-ol-1.

The prior art has taught that the addition of formic acid to, for instance, cyclooctadiene-1,5 always takes place independently of the conditions of reaction such as temperature, concentrations and mineral acid addition by means of a given, stable carbonium ion acting as the intermediary product defining compound, and that accordingly a change in the reaction conditions cannot result in a shift in the product spectrum. H. W. Gibson in an article concerning the chemistry of formic acid and its simple derivatives (Chemical Rev., Volume 69 (1969) pages 673–683, explains that in the addition of formic acid to a molecule having two or more double bonds, the addition takes place in such a manner that the most stable carbonium ion acts as the intermediary compound. This carbonium ion in the case of the cyclooctadiene-1,5 reaction is described in the above cited Cope et al reference. It is the opinion of those skilled in the art that the more stable bicyclooctyl cation is formed from the cyclooctenyl cation that is generated first. This is the explanation for the generation of bicyclooctylformate when formic acid is added as an acid catalyst to cyclooctadiene-1,5.

As disclosed by Cope et al, a long series of other by-products as well as non-identifiable resinous products of high boiling points which resist distillation are produced besides the bicyclic compounds. It was surprising therefore that in the process of the present invention higher yields should have been obtained in spite of the use of the same intermediary stages and a comparable reaction sequence.

Whereas Cope et al achieve 20% yields for short but not precisely stated times of reaction in the presence of a catalyst, the process of the present invention achieves yields which exceed 75% as referred to the converted cyclooctadiene in the absence of a catalyst. As a rule a reaction time of 10 hours suffices for the reaction of diene with formic acid. There results contradict the experience of those skilled in the art. It has been accepted by those skilled in the art that in reactions leading to products capable of further reaction, in this case the cyclooctenylformate, the selectivity decreases as the dwell time increases.

The omission of the catalyst therefore brings about surprising effects and moreover offers the advantage that the reaction product can be processed very easily, namely by direct distillation. Accordingly, the consumption of chemicals is slight, no material losses are incurred, and no ecological problems arise since the catalyst is eliminated.

The addition of the formic acid to cyclooctadiene takes place at temperatures of 50° to 200° C., preferably at 95° to 105° C. according to the present invention.

The process of the present invention is carried out on an economical basis, preferably at standard pressure, the maximum temperature then being that temperature at which the reaction mixture boils, that is in the range from 100° to 105° C. Temperatures less than 50° C. represent a limitation because they excessively lengthen the reaction time. Temperatures above 105° C. require the operation under excess pressure.

The molar ratio of cyclooctadiene to formic acid preferably is 1:0.1 to 1:10 and in particular 1:1½ to 1:6. This ratio exerts a surprising influence on the conversion as shown by the following specific examples.

The cyclooctene-4-ol-1 is obtained at a content exceeding 70%, namely 71 to 80%, determined by nuclear resonance spectroscopy.

The cyclooctene-4-ol-1 obtained by the process of the present invention is a valuable intermediate product for numerous industrial syntheses.

By GC analysis is meant gas-chromatografic analysis.

By 1H and 13C NMR spectra is meant nuclear magnetic resonance spectroscopy protons or 13C nuclears.

EXAMPLE 1

Glass apparatus consisting of a three-neck flask with stirrer, thermometer and reflux condenser is used.

1.296 Grams (12 moles) of cyclooctadiene-1,5 (99.76%) and 1.656 grams (36 moles) of formic acid (99.0%) are placed in the apparatus.

This mixture is heated under reflux for 10 hours while stirring and with a nitrogen blanket. The mixture is made to boil with a 102° C. temperature setting at the sump. After 10 hours the mixture has become homogeneous and direct distillation takes place in a 0.5 m long heated glass column filled with multifill bodies.

The first fraction separates into two phases, (a) an oil phase (359 g) and (b) a formic acid phase (1,283 g); the latter phase (b) has an acid number of 1,151.9 and accordingly consists by 94.4% of formic acid. As shown by the GC analysis, the content of cyclooctadiene-1,5 in oil phase (a) is about 70% and its conversion products (5 comp.) amount to 1.5%. As indicated by the acid number, its formic acid content is 4.2%.

The second fraction containing 36 grams and boiling between 127° and 134° C. is intermediate runnings and 88.3% consists of products generated by the addition of formic acid to cyclooctadiene-1,5.

The third fraction boiling between 134°–138° C. has 1,094 grams. As shown by the 1H and 13C NMR spectra, 75% of the third fraction consists of cyclooctene-4-ol-1-formate. The content in bicyclooctanols is 15 to 22%.

The conditions of Example 1 are tabulated below:

| | | Input: 2,907 grams | | | |
|---|---|---|---|---|---|
| Fraction No. | Boiling range °C. | Weight grams | % by weight | Pressure mbar | Return to Removal Ratio |
| 1 | 93 | (a) 359 | 12.4 | std. press. | 3:1 |
| | 103 | | | | |
| | 42 to 127 | (b) 1,283 1,642 | 44.6 57.0 | 133 | 10:1 30:1 |
| 2 | 127 to 134 | 36 | 1.3 | 133 | 30:1 |
| 3 | 134 to 138 | 1,094 | 38.0 | 133 | 30:1 5:1 |
| Residue | | 102 | 3.5 | | |
| Cold trap | | 5 | 0.2 | | |
| | | 2,879 | 100.0 | | |

From these tabulated data, an 80% conversion of cyclooctadiene-1,5 is calculated. The yield of monoformic acid ester, referred to the converted diene, is about 76% of theoretical.

The formic acid ester is transesterified in the presence of butyltitanate as the catalyst with isopropanol at temperatures of about 180° to 190° C. The isopropylformate being obtained is slowly distilled and after no more formic acid ester is obtained, first the excess isopropanol is distilled, and directly thereafter the cyclooctene-4-ol-1. The yield in the preparation of the alcohol from the formate is at about 95% of theoretical.

EXAMPLES 2 AND 3

The procedure is the same as described in Example 1. The reaction time in each case is 10 hours and the temperatures are between 98° and 102° C. Only the molar ratio of the input materials is changed. The results are listed in the table below:

| Example | Molar ratio COD: formic acid | COD conversion | Ester yield referred to the converted COD | Cyclooctene-4-ol-1 formate content |
|---|---|---|---|---|
| 2 | 1:1.5 | 36.7% | 78.8% | 72% |
| 3 | 1:6 | 99.0% | 62.8% | 80% |

(COD = cyclooctadiene-1,5)

These examples show that the molar ratio of the input materials exert a very strong influence on the conversion.

EXAMPLES 4 AND 5

The procedure is the same as in Example 1, however, the temperature was changed. The temperature is 60° C. in Example 4 and 160° C. in Example 5. Operation is in a pressurized reactor for Example 5. The table below lists the results.

| Example | Temp. °C. | Test duration (h) | COD conversion, % | Ester yield referred to converted COD, % | Cyclooctene-4-ol-1 formate content, % |
|---|---|---|---|---|---|
| 4 | 60 | 20 | 43.7 | 77.9 | 78 |
| 5 | 160 | 3 | 51.6 | 53.23 | 72 |

The reaction takes place in the manner of Example 1.

I claim:

1. A process for preparing cyclooctene-4-ol-1 consisting essentially of:
   (a) reacting cyclooctadiene-1,5 with formic acid in a ratio of 1:1.5 to 1:6 to form cyclooctenyl formate at a temperature of about 50° to 200° C. for a period of 3 to 20 hours;
   (b) separating said cyclooctenyl formate by distillation into a plurality of fractions including a first fraction having an oil phase containing cyclooctadiene-1,5 and a formic acid phase, a second fraction containing any unidentified products generated by the addition of formic acid to cyclooctadiene-1,5 and a third fraction containing cyclooctene-4-ol-1-formate;
   (c) saponifying said cyclooctene-4-ol-1-formate from said third fraction; and
   (d) separating in excess of 70% of said cyclooctene-4-ol-1 based on converted cyclooctadiene-1,5 from said formate by distillation.

2. A process for preparing cyclooctene-4-ol-1 consisting essentially of:
   (a) reacting cyclooctadiene-1,5 with formic acid in a ratio of 1:1.5 to 1:6 to form cyclooctenyl formate at a temperature of about 50° to 200° C. for a period of 3 to 20 hours;
   (b) separating said cyclooctenyl formate by distillation into a plurality of fractions including a first fraction having an oil phase containing cyclooctadiene-1,5 and a formic acid phase, a second fraction containing any unidentified products generated by the addition of formic acid to cyclooctadiene-1,5 and a third fraction containing cyclooctene-4-ol-1-formate;
   (c) transesterifying said cyclooctene-4-ol-1-formate from said third fraction with an alcohol having a low boiling point to form a formate of said alcohol and cyclooctene-4-ol-1; and
   (d) separating in excess of 70% of said cyclooctene-4-ol-1 based on converted cyclooctadiene-1,5 from said formate by distillation.

3. The process of claim 1, wherein said temperature of step (a) is 60° to 160° C.

4. The process of claim 2, wherein said temperature of step (a) is 60° to 160° C.

5. The process of claim 1, wherein said temperature of step (a) is 95° to 105° C.

6. The process of claim 2, wherein said temperature of step (a) is 95° to 105° C.

7. The process of claim 1, wherein step (a) is carried out at a boiling temperature of the reaction mixture of 100° to 105° C. at STP conditions.

8. The process of claim 2, wherein step (a) is carried out at a boiling temperature of the reaction mixture of 100° to 105° C. at STP conditions.

9. The process of claim 2, wherein said alcohol of step (c) has a boiling point between 64° and 158° C.

10. The process of claim 9, wherein said alcohol is selected from the group consisting of methanol, ethanol, propanol, isopropanol, n-butanol, iso-butanol, tert.-butanol, pentanol and hexanol.

11. The process of claim 1, including distilling of a first part of said first fraction at a temperature range of about 93° to 103° C. at STP conditions, then generating a vacuum of about 133 millibars, and completing the distillation of said first, second, and third fractions.

12. The process of claim 2, including distilling a first part of said first fraction at a temperature range of about 93° to 103° C. at STP conditions, then generating a vacuum of about 133 millibars, and completing the distillation of said first, second, and third fractions.

13. The process of claim 1, wherein said cyclooctene-4-ol-1 separated in step (d) is 71 to 80% based on converted cyclooctadiene-1,5.

14. The process of claim 2, wherein said cyclooctene-4-ol-1 separated in step (d) is 71 to 80% based on converted cyclooctadiene-1,5.

15. A process for preparing cyclooctene-4-ol-1 consisting essentially of
   (a) reacting cyclooctadiene-1,5 with formic acid in a ratio of 1:1.5 to 1:6 to form cyclooctenyl formate at a temperature of about 50° to 200° C. for a period of 3 to 20 hours;
   (b) separating said cyclooctenyl formate by distillation into a plurality of fractions including a first fraction having an oil phase with a boiling range of 93° to 103° C. and containing cyclooctadiene-1,5 and a formic acid phase with a boiling range of 42° to 127° C., a second fraction with a boiling range of 127° to 134° C. and containing any unidentified products generated by the addition of formic acid to cyclooctadiene-1,5 and a third fraction with a boiling range of 134° to 138° C. and containing cyclooctene-4-ol-1-formate, including distilling a first part of said first fraction at a temperature range of about 93° to 103° C. at STP conditions, then generating a vacuum of about 133 millibars, and completing the distillation of said first, second, and third fractions;
   (c) saponifying said cyclooctene-4-ol-1-formate from said third fraction; and
   (d) separating in excess of 70% of said cyclooctene-4-ol-1 based on converted cyclooctadiene-1,5 from said formate by distillation.

16. A process for preparing cyclooctene-4-ol-1 consisting essentially of:
   (a) reacting cyclooctadiene-1,5 with formic acid in a ratio of 1:1.5 to 1:6 to form cyclooctenyl formate at a temperature of about 50° to 200° C. for a period of 3 to 20 hours;
   (b) separating said cyclooctenyl formate by distillation into a plurality of fractions including a first fraction having an oil phase with a boiling range of 93° to 103° C. and containing cyclooctadiene-1,5 and a formic acid phase with a boiling range of 42° to 127° C., a second fraction with a boiling range of 127°–134° C. and containing any unidentified products generated by the addition of formic acid to cyclooctadiene-1,5 and a third fraction with a boiling range of 134° to 138° C. and containing cyclooctene-4-ol-1-formate, including distilling a first part of said first fraction at a temperature range of 93° to 103° C. at STP conditions, then generating a vacuum of about 133 millibars, and completing the distillation of said first, second, and third fractions;
   (c) transesterifying said cyclooctene-4-ol-1-formate from said third fraction with an alcohol having a low boiling point to form a formate of said alcohol and cyclooctene-4-ol-1; and
   (d) separating in excess of 70% of said cyclooctene-4-ol-1 based on converted cyclooctadiene-1,5 from said formate by distillation.

* * * * *